United States Patent [19]

Aristoff

[11] 4,346,041
[45] Aug. 24, 1982

[54] COMPOSITION AND PROCESS

[75] Inventor: Paul A. Aristoff, Portage, Mich.

[73] Assignee: The Upjohn Company, Kalamazoo, Mich.

[21] Appl. No.: 219,198

[22] Filed: Dec. 22, 1980

Related U.S. Application Data

[63] Continuation-in-part of Ser. No. 125,608, Feb. 28, 1980, Pat. No. 4,338,457.

[51] Int. Cl.$^3$ ............................................. C07C 49/633
[52] U.S. Cl. .................................... 549/498; 542/426; 542/427; 549/62; 549/78; 556/436; 568/327; 568/374
[58] Field of Search ................. 568/374, 327; 542/426, 542/429; 260/347.8, 345.9 P, 62; 549/78; 556/436

[56] References Cited

U.S. PATENT DOCUMENTS 4,225,507  9/1980  Sih .................................. 260/346.22

OTHER PUBLICATIONS

McComie, Protective Groups in Organic Chemistry, pp. 95–120, (1973).

*Primary Examiner*—Robert Gerstl
*Attorney, Agent, or Firm*—L. Ruth Hattan; Robert A. Armitage

[57] ABSTRACT

The present specification provides novel analogs of carbacyclin ($CBA_2$), 6a-carba-prostacyclin (6a-carba-$PGI_2$), which have pronounced prostacyclin-like pharmacological activity, e.g., as platelet antiaggregatory agents. Specifically the novel chemical analogs of $CBA_2$ are those substituted by fluoro (C-5), alkyl (C-9), interphenylene (C-5), and methano (C-6a,9). Further provided are benzindene analogs of $CBA_2$ and substituted forms thereof, i.e., 9-deoxy-2',9-methano (or 2',9-metheno)-3-oxa-4,5,6-trinor-3,7-(1',3'-interphenylene)-$PGF_1$ compounds. Also provided are a variety of novel chemical intermediates, e.g., substituted bicyclo[3.3.-0]octane intermediates, and chemical process utilizing such intermediates which are useful in the preparation of the novel $CBA_2$ analogs.

1 Claim, No Drawings

COMPOSITION AND PROCESS

This application is a continuation-in-part of Ser. No. 125,608, filed Feb. 28, 1980, and now U.S. Pat. No. 4,338,457.

DESCRIPTION

BACKGROUND OF THE INVENTION

The present invention relates to novel compositions of matter and novel processes for preparing these compositions of matter. Moreover, there are provided novel methods by which certain of these novel compositions of matter are employed for pharmacologically useful purposes. Further there are provided novel chemical intermediates for preparing these compositions of matter.

The present invention is specifically concerned with novel analogs of prostacyclin or $PGI_2$. Specifically, the present invention is concerned with analogs of carbacyclin modified at the C-5 or C-9 position, e.g., C-5 interphenylene analogs of carbacyclin, 5-fluoro analogs of carbacyclin, $9\beta$-alkyl analogs of carbacyclin, C-6a,9 tricyclic (cyclopropyl) analogs of carbacyclin, and combinations thereof as well as novel benzindene analogs thereof.

Prostacyclin is an endogenously produced compound in mammalian species, being structurally and biosynthetically related to the prostaglandins (PG's). In particular, prostacyclin exhibits the structure and carbon atom numbering of formula I when the C-5,6 positions are unsaturated. For convenience, prostacyclin is often referred to simply as "$PGI_2$". Carbacyclin, 6a-carba-$PGI_2$, exhibits the structure and carbon atom numbering indicated in formula II when the C-5,6 positions are unsaturated. Likewise, for convenience, carbacyclin is referred to simply as "$CBA_2$".

A stable partially saturated derivative of $PGI_2$ is $PGI_1$ or 5,6-dihydro-$PGI_2$ when the C-5,6 positions are saturated, depicted with carbon atom numbering in formula II when the C-5,6 positions are saturated. The corresponding 5,6-dihydro-$CBA_2$ is $CBA_1$, depicted in formula II.

As is apparent from inspection of formulas I and II, prostacyclin and carbacyclin may be trivially named as derivatives of PGF-type compounds, e.g., $PGF_2\alpha$ of formula III. Accordingly, prostacyclin is trivially named 9-deoxy-6,9$\alpha$-epoxy-(5Z)-5,6-didehydro-$PGF_1$ and carbacyclin is named 9-deoxy-6,9$\alpha$-methano-(5E)-5,6-didehydro-$PGF_1$. For description of prostacyclin and its structural identification, see Johnson, et. al., Prostaglandins 12:915 (1976).

For convenience, the novel prostacyclin or carbacyclin analogs will be referred to by the trivial, art-recognized system of nomenclature described by N. A. Nelson, J. Med. Chem. 17:911 (1974) for prostaglandins. Accordingly, all of the novel prostacyclin derivatives herein will be named as 9-deoxy-$PGF_1$-type compounds, $PGI_2$ derivatives, or preferably as $CBA_1$ or $CBA_2$ derivatives.

In the formulas herein, broken line attachments to a ring indicate substituents in the "alpha" ($\alpha$) configuration, i.e., below the plane of said ring. Heavy solid line attachments to a ring indicate substituents in the "beta" ($\beta$) configuration, i.e., above the plane of said ring. The use of wavy lines ($\sim$) herein will represent attachment of substituents in the alpha or beta configuration or attached in a mixture of alpha and beta configurations. Alternatively wavy lines will represent either an E or Z geometric isomeric configuration or the mixture thereof.

A side chain hydroxy at C-15 in the formulas herein is in the S or R configuration as determined by the Cahn-Ingold-Prelog sequence rules, J. Chem. Ed. 41:16 (1964). See also Nature 212:38 (1966) for discussion of the stereochemistry of the prostaglandins which discussion applies to the novel prostacyclin or carbacyclin analogs herein. Molecules of prostacyclin and carbacyclin each have several centers of asymmetry and therefore can exist in optically inactive form or in either of two enantiomeric (optically active) forms, i.e., the dextrorotatory and laveorotatory forms. As drawn, the formula for $PGI_2$ corresponds to that endogenously produced in the mammalian species. In particular, refer to the stereochemical configuration at C-8 ($\alpha$), C-9 ($\alpha$), C-11 ($\alpha$) and C-12 ($\beta$) of endogenously produced prostacyclin. The mirror image of the above formula for prostacyclin represents the other enantiomer. The racemic form of prostacyclin contains equal numbers of both enantiomeric molecules.

For convenience, reference to prostacyclin and carbacyclin will refer to the optically active form thereof. Thus, with reference to prostacyclin, reference is made to the form thereof with the same absolute configuration as that obtained from the mammalian species.

The term "prostacyclin-type" product, as used herein, refers to any cyclopentane derivative herein which is useful for at least one of the same pharmacological purposes for which prostacyclin is employed. A formula as drawn herein which depicts a prostacyclin-type product or an intermediate useful in the preparation thereof, represents that particular stereoisomer of the prostacyclin-type product which is of the same relative stereochemical configuration as prostacyclin obtained from mammalian tissues or the particular stereoisomer of the intermediate which is useful in preparing the above stereoisomer of the prostacyclin type product.

The term "prostacyclin analog" or "carbacyclin analog" represents that stereoisomer of a prostacyclin-type product which is of the same relative stereochemical configuration as prostacyclin obtained from mammalian tissues or a mixture comprising stereoisomer and the enantiomers thereof. In particular, where a formula is used to depict a prostacyclin type product herein, the term "prostacyclin analog" or "carbacyclin analog" refers to the compound of that formula or a mixture comprising that compound and the enantiomer thereof.

PRIOR ART

Carbacyclin and closely related compounds are known in the art. See Japanese Kokia 63,059 and 63,060, also abstracted respectively as Derwent Farmdoc CPI Numbers 48154B/26 and 48155B/26. See also British published specifications 2,012,265 and German Offenlungsschrift 2,900,352, abstracted as Derwent Farmdoc CPI Number 54825B/30. See also British published applications Nos. 2,017,699, 2,014,143 and 2,013,661.

The synthesis of carbacyclin and related compounds is also reported in the chemical literature, as follows: Morton, D. R., et al., J. Organic Chemistry, 44:2880 (1979); Shibasaki, M., et al. Tetrahedron Letters, 433–436 (1979); Kojima, K., et al., Tetrahedron Letters, 3743–3746 (1978); Nicolaou, K. C., et al., J. Chem. Soc., Chemical Communications, 1067–1068 (1978); Sugie, A., et al., Tetrahedron Letters 2607–2610 (1979); Shibasaki, M., Chemistry Letters, 1299–1300 (1979), and Hayashi, M., Chem. Lett. 1437–40 (1979); and Li, Tsung-tee, "A Facile Synthesis of 9(O)-Methano-prostacyclin", Abstract No. 378, (Organic Chemistry), and P. A. Aristoff, "Synthesis of 6a-Carbaprostacyclin I₂", Abstract No. 236 (Organic Chemistry) both at Abstract of Papers (Part II) Second Congress of the North American Continent, San Francisco, California (Las Vegas, Nevada), USA, 24–29 August 1980.

7-Oxo and 7-hydroxy-CBA$_2$ compounds are apparently disclosed in U.S. Pat. No. 4,192,891. 19-Hydroxy-CBA$_2$ compounds are disclosed in U.S. Ser. No. 54,811, filed July 5, 1979. CBA$_2$ aromatic esters are disclosed in U.S. Pat. No. 4,180,657. 11-Deoxy-$\Delta^{10}$- or $\Delta^{11}$-CBA$_2$ compounds are described in Japanese Kokai 77/24,865, published Feb. 24, 1979.

SUMMARY OF THE INVENTION

The present specification particularly provides:
(a) a carbacyclin intermediate of formula IV, V, VI, VII, VIII, or IX; and
(b) a carbacyclin analog of formula X or XI; wherein g is 0, 1, 2, or 3;
wherein n is one or 2;
wherein $L_1$ is $\alpha$-$R_3$:$\beta$-$R_4$, $\alpha$-$R_4$:$\beta$-$R_3$, or a mixture of $\alpha$-$R_3$:$\beta$-$R_4$ and $\alpha$-$R_4$:$\beta$-$R_3$, wherein $R_3$ and $R_4$ are hydrogen, methyl, or fluoro, being the same or different, with the proviso that one of $R_3$ and $R_4$ is fluoro only when the other is hydrogen or fluoro;
wherein $M_1$ is $\alpha$-OH:$\beta$-$R_5$ or $\alpha$-$R_5$:$\beta$-OH, wherein $R_5$ is hydrogen or methyl;
wherein $M_6$ is $\alpha$-$OR_{10}$:$\beta$-$R_5$ or $\alpha$-$R_5$:$\beta$-$OR_{10}$, wherein $R_5$ is hydrogen or methyl and $R_{10}$ is an acid hydrolyzable protective group;
wherein $R_7$ is
(1) —$C_mH_{2m}$—$CH_3$, wherein m is an integer from one to 5, inclusive,
(2) phenoxy optionally substituted by one, two or three chloro, fluoro, trifluoromethyl, ($C_1$–$C_3$)alkyl, or ($C_1$–$C_3$)alkoxy, with the proviso that not more than two substituents are other than alkyl, with the proviso that $R_7$ is phenoxy or substituted phenoxy, only when $R_3$ and $R_4$ are hydrogen or methyl, being the same or different,
(3) phenyl, benzyl, phenylethyl, or phenylpropyl optionally substituted on the aromatic ring by one, two or three chloro, fluoro, trifluoromethyl, ($C_1$–$C_3$)alkyl, or ($C_1$–$C_3$)alkoxy, with the proviso that not more than two substituents are other than alkyl,
(4) cis—CH=CH—$CH_2$—$CH_3$,
(5) —$(CH_2)_2$—CH(OH)—$CH_3$, or
(6) —$(CH_2)_3$—CH=C$(CH_3)_2$;
wherein —C($L_1$)—$R_7$ taken together is
(1) ($C_4$–$C_7$)cycloalkyl optionally substituted by one to 3 ($C_1$–$C_5$) alkyl;
(2) 2-(2-furyl)ethyl,
(3) 2-(3-thienyl)ethoxy, or
(4) 3-thienyloxymethyl;
wherein $R_8$ is hydroxy, hydroxymethyl., or hydrogen;
wherein $R_{15}$ is hydrogen or fluoro;
wherein $R_{16}$ is hydrogen or $R_{16}$ and $R_{17}$ taken together are —$CH_2$— or $R_{16}$ and $R_{47}$ taken together form a second valence bond between C-6a and C-9 or are —$CH_2$—;
wherein $R_{17}$ is as defined above or is
(1) hydrogen, or
(2) ($C_1$–$C_4$)alkyl;

wherein $R_{18}$ is hydrogen, hydroxy, hydroxymethyl, —$OR_{10}$ or —$CH_2OR_{10}$, wherein $R_{10}$ is an acid-hydrolyzable protective group; wherein
(1) $R_{20}$, $R_{21}$, $R_{22}$, $R_{23}$, and $R_{24}$ are all hydrogen with $R_{22}$ being either $\alpha$-hydrogen or $\beta$-hydrogen,
(2) $R_{20}$ is hydrogen, $R_{21}$ and $R_{22}$ taken together form a second valence bond between C-9 and C-6a, and $R_{23}$ and $R_{24}$ taken together form a second valence bond between C-8 and C-9 or are both hydrogen, or
(3) $R_{22}$, $R_{23}$, and $R_{24}$ are all hydrogen, with $R_{22}$ being either $\alpha$-hydrogen or $\beta$-hydrogen, and
(a) $R_{20}$ and $R_{21}$ taken together are oxo, or
(b) $R_{20}$ is hydrogen and $R_{21}$ is hydroxy, being $\alpha$-hydroxy or $\beta$-hydroxy;
wherein $R_{27}$ is the same as $R_7$ except that —$(CH_2)_2$—CH(OH)—$CH_3$ is —$(CH_2)_2$—CH($OR_{11}$)—$CH_3$;
wherein $R_{32}$ is hydrogen or $R_{31}$, wherein $R_{31}$ is a hydroxyl hydrogen replacing group;
wherein $R_{33}$ is —CHO or —$CH_2OR_{32}$, wherein $R_{32}$ is as defined above;
wherein $R_{47}$ is as defined above or is
(1) ($C_1$–$C_4$)alkyl, or
(2) —$CH_2OH$;
wherein $X_1$ is
(1) —$COOR_1$, wherein $R_1$ is
(a) hydrogen,
(b) ($C_1$–$C_{12}$)alkyl,
(c) ($C_3$–$C_{10}$)cycloalkyl,
(d) ($C_7$–$C_{12}$)aralkyl,
(e) phenyl, optionally substituted with one, 2 or 3 chloro or ($C_1$–$C_3$)alkyl,
(f) phenyl substituted in the para position by
(i) —NH—CO—$R_{25}$,
(ii) —CO—$R_{26}$,
(iii) —O—CO—$R_{54}$, or
(iv) —CH=N—NH—CO—$NH_2$ wherein $R_{25}$ is methyl, phenyl, acetamidophenyl, benzamidophenyl, or —$NH_2$; $R_{26}$ is methyl, phenyl, —$NH_2$, or methoxy; and $R_{54}$ is phenyl or acetamidophenyl; inclusive, or
(g) a pharmacologically acceptable cation;
(2) —$CH_2OH$,
(3) —$COL_4$, wherein $L_4$ is
(a) amino of the formula —$NR_{51}R_{52}$, wherein $R_{51}$ and $R_{52}$ are
(i) hydrogen,
(ii) ($C_1$–$C_{12}$)alkyl,
(iii) ($C_3$–$C_{10}$)cycloalkyl,
(iv) ($C_7$–$C_{12}$)aralkyl,
(v) phenyl, optionally substituted with one, 2 or 3 chloro, ($C_1$–$C_3$)alkyl, hydroxy, carboxy, ($C_2$–$C_5$)alkoxycarbonyl, or nitro,
(vi) ($C_2$–$C_5$)carboxyalkyl,
(vii) ($C_2$–$C_5$)carbamoylalkyl,
(viii) ($C_2$–$C_5$)cyanoalkyl,
(ix) ($C_3$–$C_6$)acetylalkyl,
(x) ($C_7$–$C_{11}$)benzoalkyl, optionally substituted by one, 2 or 3 chloro, ($C_1$–$C_3$)alkyl, hydroxy, ($C_1$–$C_3$)alkoxy, carboxy, ($C_2$–$C_5$)alkoxycarbonyl, or nitro,
(xi) pyridyl, optionally substituted by one, 2 or 3 chloro, ($C_1$–$C_3$)alkyl, or ($C_1$–$C_3$)alkoxy,
(xii) ($C_6$–$C_9$)pyridylalkyl optionally substituted by one, 2 or 3 chloro, ($C_1$–$C_3$)alkyl, hydroxy, or ($C_1$–$C_3$)alkyl,
(xiii) ($C_1$–$C_4$)hydroxyalkyl,
(xiv) ($C_1$–$C_4$)dihydroxyalkyl,
(xv) ($C_1$–$C_4$)trihydroxyalkyl, with the further proviso that not more than one of $R_{51}$ and $R_{52}$ is other than hydrogen or alkyl, (b) cycloamino selected from the group consisting of pyrolidino, piperidino, morpholino, piperazino, hexamethyleneimino, pyrrolino, or 3,4-didehydropiperidinyl optionally substituted by one or 2 ($C_1$-$C_{12}$)alkyl of one to 12 carbon atoms, inclusive, (c) carbonylamino of the formula $-NR_{53}COR_{51}$, wherein $R_{23}$ is hydrogen or ($C_1$-$C_4$)alkyl and $R_{51}$ is other than hydrogen, but otherwise as defined above, (d) sulfonylamino of the formula $-NR_{53}SO_2R_{51}$, wherein $R_{21}$ and $R_{23}$ are as defined in (c), (4) $-CH_2NL_2L_3$, wherein $L_2$ and $L_3$ are hydrogen or ($C_1$-$C_4$)alkyl, being the same or different, or the pharmacologically acceptable acid addition salts thereof when $X_1$ is $-CH_2NL_2L_3$, wherein $Y_1$ is trans$-CH=CH-$, cis$-CH=CH-$, $-CH_2CH_2-$, or $-C\equiv C-$;

wherein $Z_1$ is (1) $-CH_2-(CH_2)_f-C(R_2)_2$, wherein $R_2$ is hydrogen or fluoro and f is zero, one, 2, or 3, (2) trans$-CH_2-CH=CH-$, (3) $-(Ph)-(CH_2)_g-$, wherein (Ph) is 1,2-, 1,3-, or 1,4-phenylene and g is zero, one, 2, or 3;

wherein $Z_4$ is $-CH_2-$ or $-(CH_2)_f-CF_2$, wherein f is as defined above;

with the overall proviso that (1) $R_{15}$, $R_{16}$, and $R_{17}$ are all hydrogen only when $Z_1$ is $-(Ph)-(CH_2)_g-$, and (2) $Z_1$ is $-(Ph)-(CH_2)_g-$ only when $R_{15}$ is hydrogen.

The detailed description, preparation, and use of the present invention is incorporated herein by reference from U.S. Pat. No. 4,306,075 beginning at column 5, line 36 through column 95, line 43.

I claim:

1. The carbacyclin intermediate of formula IV or V:

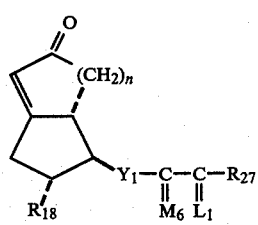

IV

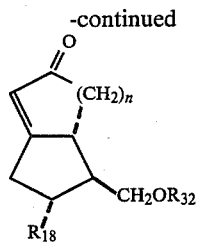

V wherein n is one or 2;

wherein $L_1$ is α-$R_3$:β-$R_4$, α-$R_4$:β-$R_3$, or a mixture of α-$R_3$:β-$R_4$ and α-$R_4$:β-$R_3$, and wherein $R_3$ and $R_4$ are hydrogen, methyl, or fluoro, being the same or different, with the proviso that one of $R_3$ and $R_4$ is fluoro only when the other is hydrogen or fluoro;

wherein $M_6$ is α-$OR_{10}$:β-$R_5$ or α-$R_5$:β-$OR_{10}$, wherein $R_5$ is hydrogen or methyl and $R_{10}$ is an acid hydrolyzable protective group;

wherein $R_{27}$ is (1) $-C_mH_{2m}-CH_3$, wherein m is an integer from one to 5, inclusive, (2) phenoxy optionally substituted by one, two or three chloro, fluoro, trifluoromethyl, ($C_1$-$C_3$)alkyl, or ($C_1$-$C_3$)alkoxy, with the proviso that not more than two substituents are other than alkyl, with the proviso that $R_{27}$ is phenoxy or substituted phenoxy, only when $R_3$ and $R_4$ are hydrogen or methyl, being the same or different, (3) phenyl, benzyl, phenylethyl, or phenylpropyl optionally substituted on the aromatic ring by one, two or three chloro, fluoro, trifluoromethyl, ($C_1$-$C_3$)alkyl, or ($C_1$-$C_3$)alkoxy, with the proviso that not more than two substituents are other than alkyl, (4) cis$-CH=CH-CH_2-CH_3$, (5) $-(CH_2)_2-CH(OR_{10})-CH_3$, wherein $R_{10}$ is as defined above, or (6) $-(CH_2)_3-CH=C(CH_3)_2$;

wherein $-C(L_1)-R_{27}$ taken together is (1) ($C_4$-$C_7$)cycloalkyl optionally substituted by one to 3 ($C_1$-$C_5$)alkyl;

(2) 2-(2-furyl)ethyl, (3) 2-(3-thienyl)ethoxy, or (4) 3-thienyloxymethyl;

wherein $R_{18}$ is hydrogen, hydroxy, hydroxymethyl, $-OR_{10}$ or $-CH_2OR_{10}$, wherein $R_{10}$ is an acid-hydrolyzable protective group;

wherein $R_{32}$ is hydrogen or $R_{31}$, wherein $R_{31}$ is a hydroxyl hydrogen protective group; and wherein $Y_1$ is trans$-CH=CH-$, cis$-CH=CH-$, $-CH_2CH_2-$, or $-C\equiv C-$.

* * * * *